US006666826B2

(12) United States Patent
Salo et al.

(10) Patent No.: US 6,666,826 B2
(45) Date of Patent: Dec. 23, 2003

(54) METHOD AND APPARATUS FOR MEASURING LEFT VENTRICULAR PRESSURE

(75) Inventors: Rodney Salo, Fridley, MN (US); Angelo Auricchio, Magdeburg (DE)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 10/038,936

(22) Filed: Jan. 4, 2002

(65) Prior Publication Data

US 2003/0130581 A1 Jul. 10, 2003

(51) Int. Cl.[7] ............................. A61B 5/02; A61N 1/18
(52) U.S. Cl. ...................... 600/485; 600/486; 600/509; 607/23
(58) Field of Search ....................... 600/485, 481, 600/486, 488, 508, 509; 607/9, 17, 23, 2, 1

(56) References Cited

U.S. PATENT DOCUMENTS

| 3,995,623 A | | 12/1976 | Blake et al. |
| 4,485,813 A | * | 12/1984 | Anderson et al. ........... 600/488 |
| 4,674,518 A | | 6/1987 | Salo |
| 5,083,563 A | | 1/1992 | Collins |
| 5,129,394 A | | 7/1992 | Mehra |
| 5,324,326 A | | 6/1994 | Lubin |
| 5,464,434 A | | 11/1995 | Alt |
| 5,755,766 A | | 5/1998 | Chastain et al. |
| 6,136,021 A | | 10/2000 | Tockman et al. |
| 6,198,952 B1 | | 3/2001 | Miesel |
| 6,280,389 B1 | | 8/2001 | Ding et al. |
| 6,309,350 B1 | | 10/2001 | VanTassel et al. |
| 6,398,738 B1 | * | 6/2002 | Millar ........................ 600/486 |

OTHER PUBLICATIONS

H. Kim and K. Chun. "Integrated MEMS for Pressure Transponder." *Transducers '97*, vol. 2, pp. 1011–1014. Jun. 16, 1997. 1997 International Conference on Solid–Stator Sensor and Actuators. Chicago, IL.

* cited by examiner

*Primary Examiner*—Max F. Hindenburg
*Assistant Examiner*—Navin Natnithithadha
(74) *Attorney, Agent, or Firm*—Crawford Maunu PLLC

(57) ABSTRACT

A body implantable system employs a lead system having at least one electrode and at least one pressure transducer at a distal end. The lead system is implanted within a patient's heart in a coronary vein of the left ventricle. The lead system includes an occlusion device at a distal end to occlude flow in the coronary vein. The pressure transducer is attached to a catheter that is disposed within an open lumen of the lead system. The pressure transducer senses a coronary vein pressure, the coronary vein pressure being proportional to the left ventricular pressure. The sensed coronary vein pressure gives indications of hemodynamic state of the left ventricle, and measured coronary vein pressure can be used to change a signal sent to the electrode to adaptively pace the patient's heart. The body implantable system can further utilize a right ventricular pressure measurement in concert with the left ventricular pressure measurement to modify pacing therapy parameters.

36 Claims, 4 Drawing Sheets

METHOD AND APPARATUS FOR MEASURING LEFT VENTRICULAR PRESSURE

FIELD OF THE INVENTION

The invention relates to a method and apparatus for measuring left ventricular blood pressure, and more particularly to measuring left ventricular pressure from a pacing/defibrillation lead implanted in a branch vein of the coronary sinus. The measured left ventricular pressure may be used to adaptively control a pacing or defibrillation lead.

BACKGROUND OF THE INVENTION

Heart disease (cardiomyopathy) can cause a patient to exhibit symptoms of congestive heart failure (CHF). CHF is a result of the weakening of the heart's cardiac function characterized by reduced pumping capacity and efficiency. Chronic cardiac rhythm problems can also be the result of cardiomyopathy. The modification of the heart's structure that causes the reduction in pumping capacity also causes modification of the heart's electrical characteristics. The heart's electrical pathways can become stretched out of shape and chemically damaged. This makes arrhythmias much more likely to occur in CHF patients.

Implantation of a pacemaker is a preferred method of treatment for arrhythmias in CHF patients. Although many types of heart problems may require a pacer, one method of treatment suited for CHF patients is known as cardiac resynchronization therapy (CRT). CRT uses a pacemaker with multiple pacing leads to coordinate the heart's four chambers to act together in a sequence that will pump blood more efficiently.

It is likely that CRT candidates will have various forms of cardiomyopathy, and these patients may exhibit other measurable symptoms of reduced cardiac function besides arrhythmia. The reduced cardiac function of the heart is taken into account when applying CRT in order to tailor the treatment based on the needs of a particular patient. Various external factors must also be taken into account by the pacing system, one of those factors being the current state of activity of the patient.

Rate adaptive pacemakers are currently used that can estimate body activity by detecting body activity or breathing rate and depth, and therefore modify the pacing rate applied to the heart. These indicators can give a rough estimate of metabolic demand for a given patient. It would be beneficial to have more accurate measures of metabolic demand, especially measures that can determine the pumping capacity and pumping efficiency of a heart in order to measure and improve the efficacy of the therapy for the CHF patient.

For the reasons stated above, and for other reasons stated below which will become apparent to those skilled in the art upon reading the present specification, there is a need in the art for improved ventricular monitoring and therapy control. There exists a further need for a pacing system that provides a means of measuring cardiac workload and efficiency in order to offer more effective treatment for CHF patients. The present invention fulfills these and other needs, and provides several advantages over prior systems and techniques.

SUMMARY OF THE INVENTION

The present invention is directed to a method and apparatus employing a pressure sensor in a body implantable pacing system. According to one embodiment of the present invention, a body implantable system includes a lead system having an open lumen, at least one electrode, and an occlusion device at a distal end of the lead system. A sensing catheter is movably disposed within the open lumen of the lead system. A distal tip of the sensing catheter extends beyond a distal tip of the lead system. The sensing catheter includes at least one pressure transducer at a distal end of the sensing catheter. A detection/energy delivery system is coupled to the lead system. The detection/energy delivery system senses ventricular rhythms from the electrode(s), senses pressure from the pressure transducer(s), and delivers an electrical signal to the electrode(s).

In one configuration, the pressure transducer includes a capacitive pressure sensor. In other configurations, the pressure transducer includes a piezoresistive pressure sensor, a micro-electrical-mechanical system (MEMS) pressure sensor and/or a resistive pressure sensor.

The detection/energy system may be configured to deliver a synchronized electrical signal to the electrode(s) for resynchronization therapy. The detection/energy system may also use a measured pressure from the pressure transducer(s) to adaptively modify the electrical signal sent to electrode(s).

The occlusion device of the lead system may include an increased diameter of the lead system at the distal end of the lead system. The occlusion device may also include an inflatable member at the distal end of the lead system. The inflatable member can include an absorbable material, the absorbable material inflating upon contact with a fluid. In another configuration, the inflatable member may inflate by injection of a fluid into the lead system.

According to another embodiment of the present invention, a method of pacing a patient's heart involves implanting a lead system into a coronary vein of the patient's heart. The lead system includes an open lumen, at least one electrode, and an occlusion device at a distal end of the lead system, the occlusion device occluding blood flow in the vein.

The method further involves introducing a sensing catheter within the open lumen of the lead system until a distal tip of the sensing catheter extends beyond a distal tip of the lead system. The sensing catheter includes at least one pressure transducer at a distal end of the sensing catheter. Ventricular electrical rhythms are measured from the electrode(s) to deliver a synchronized electrical signal to the electrode(s). A vein pressure is measured from the pressure transducer to adaptively modify the synchronized electrical signal.

Modifying the synchronized electrical signals can further involve measuring a timing between the measured coronary vein pressure and the measured ventricular electrical rhythms. Modifying the synchronized electrical signal can further involve modifying the synchronized electrical signal to minimize the pre-ejection period.

In one aspect of the method, a scaling factor is calculated between a measured coronary vein pressure and a left ventricular pressure. The scaling factor is applied before adaptively modifying the rate of the synchronized electrical signals.

According to another embodiment of the present invention, a method of pacing a patient's heart involves implanting a first lead system into a coronary vein of the patient's heart and a second lead system into a chamber of the patient's heart. The first and second lead systems each include at least one electrode and at least one pressure transducer at respective distal ends of the lead systems.

The method further involves measuring ventricular electrical rhythms from the electrodes of the first and second lead systems to deliver synchronized electrical signals to the electrodes of the first and second lead systems. A coronary vein pressure is measured from the pressure transducer(s) of the first lead system and a heart chamber pressure is measured from the pressure transducer(s) of the second lead system to adaptively modify the synchronized electrical signals.

In one aspect of the method, the second lead system is implanted in the right ventricle, and adaptively modifying the synchronized electrical signals further involves measuring a right ventricular pressure from the pressure transducer(s) of the second lead system. Adaptively modifying the synchronized electrical signals can further involve adaptively modifying the synchronized electrical signals to minimize an area of a PP Loop derived from the measured right ventricular pressure and the measured coronary vein pressure.

In another aspect of the method, modifying the synchronized electrical signals can further involve measuring a timing between the measured coronary vein pressure and the measured ventricular electrical rhythms. Modifying the synchronized electrical signal can further involve modifying the synchronized electrical signal to minimize the pre-ejection period.

Modifying the synchronized electrical signals can further involve measuring a timing between the measured heart chamber pressure and the measured ventricular electrical rhythms. Modifying the synchronized electrical signal can further involve modifying the synchronized electrical signal to minimize an electromechanical timing period.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
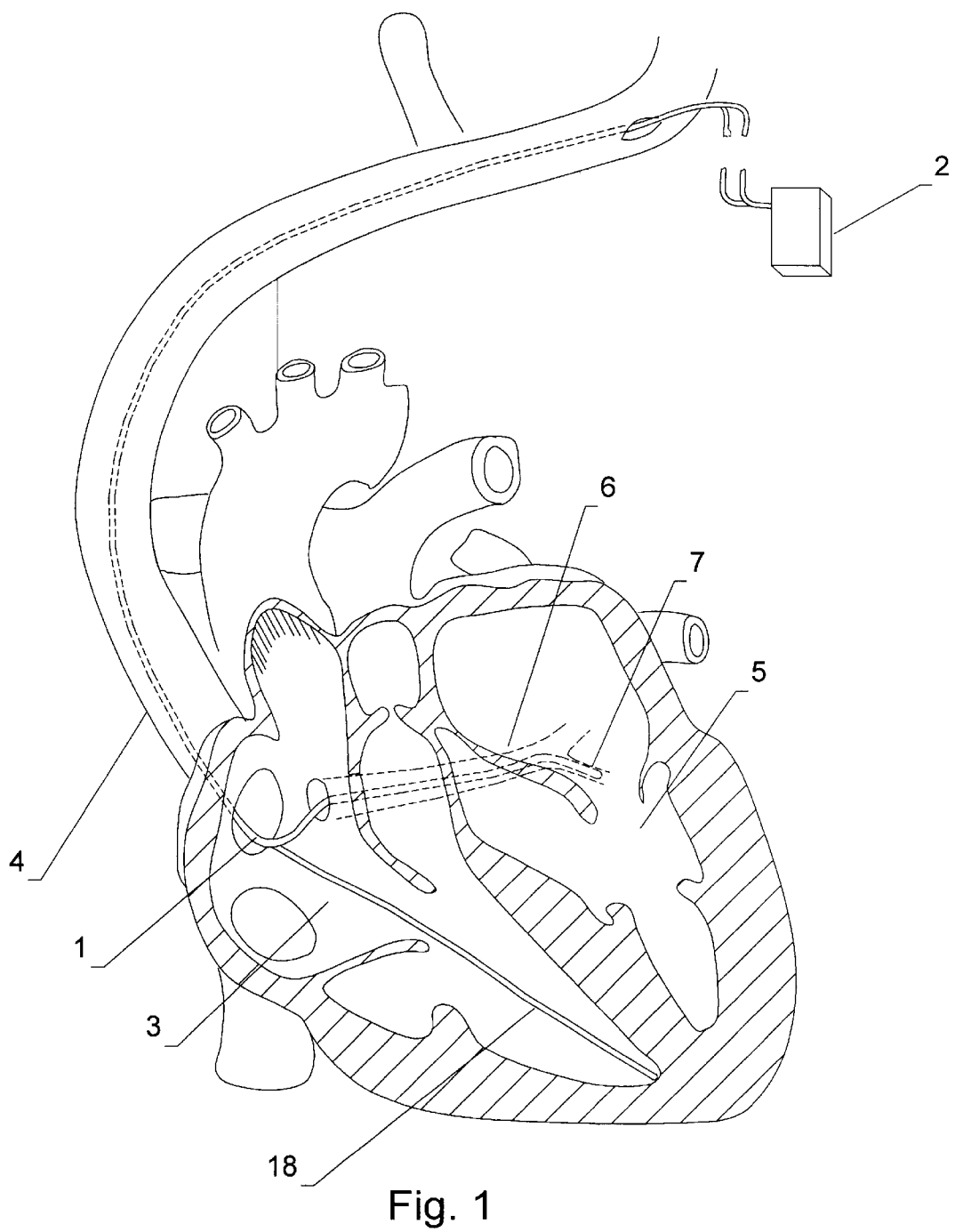
FIG. 1 is a view of the heart showing an apparatus according to the present invention implanted in the coronary sinus.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF THE VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

Various measures have been developed to characterize reduced cardiac function. One such measure is hemodynamic state, which can be loosely defined as the physics of blood flow in the circulation system. Estimating hemodynamic state includes measuring physical properties of blood such as pressure and temperature. The measurements can be taken from various chambers within the heart, including the left and right ventricles.

Hemodynamic measurements from the left ventricle are considered particularly useful, although placing devices in the left ventricle or within myocardial tissue is considered risky. Thrombus formed on implanted devices can break loose and travel to the brain causing a stroke or blockage of other blood vessels. The relatively high pressure in the left ventricle also poses the risk of hemorrhage at penetration points of the implanted device.

Given that hemodynamic parameters can be useful and accurate indicators of heart performance, the hemodynamic parameters can be beneficially applied to adaptively change therapy parameters, for example, of a cardiac pacing or defibrillation system. Further, analyzing hemodynamic state can provide a pacing system with the ability to measure and adapt to heart activity over a long period of time in order to measure and improve the efficacy of the pacing treatment for the CHF patient.

A system according to the present invention uses a pressure reading obtained from a coronary vein in the left ventricle to provide an estimate of left ventricular pressure (LVP). The LVP is generally much more indicative of cardiac function than right ventricular pressure. The left ventricular end diastolic pressure (LVEDP) is an especially important measure used to evaluate hemodynamic state. LVEDP can be measured from a coronary vein without exposing the patient to the risks involved in obtaining direct readings from the left ventricle or left atrium.

Turning now to FIG. 1, a system according to the present invention is shown deployed within a heart. The system includes a lead system 1 that is designed for implantation in a coronary vein for purposes of cardiac resynchronization therapy (CRT). The lead system 1 is coupled to a detection/energy delivery system 2 that actively measures and controls the implanted lead system to correct for electrical activation anomalies of the heart.

The detector/energy delivery system 2 typically includes a power supply and programmable circuit (e.g., microprocessor) coupled to an analog to digital (A-D) converter. Various lead system devices, such as electrodes and pressure sensors, can interface to the A-D converter for sensing/data collection. Alternatively, analog conditioning (e.g., filtering) may be applied to sensor signals before interfacing with the A-D converter. The detector/energy delivery system 2 also utilizes an energy delivery system. The energy delivery system may include charge capacitors and signal conditioning circuitry known in the art. The energy system may interface to the programmable circuit through a D-A converter.

A system according to the present invention may also be adapted for monitoring purposes only, in which case the detector/energy delivery system 2 may not require an energy delivery system. Further, although the detector/energy delivery system 2 is typically implantable, it can be appreciated that a detector/energy delivery system 2 can be externally located, in whole or in part, in some applications, such as for a temporary installation or in clinical testing.

The lead system 1 is implanted into the coronary sinus using various techniques. One such technique, as illustrated in FIG. 1, involves creating an opening in a percutaneous access vessel such as the left subclavian or left cephalic vein. The pacing lead is guided into the right atrium 3 of the heart via the superior vena cava 4. From the right atrium 3, the lead system 1 is sent into the coronary sinus ostium. The ostium is the opening of the coronary sinus 6 into the right atrium 3. The lead system 1 is guided through the coronary sinus 6 to a coronary vein 7 of the left ventricle 5. A distal end of the lead system 1 is lodged into the coronary vein 7.

Figure 2:
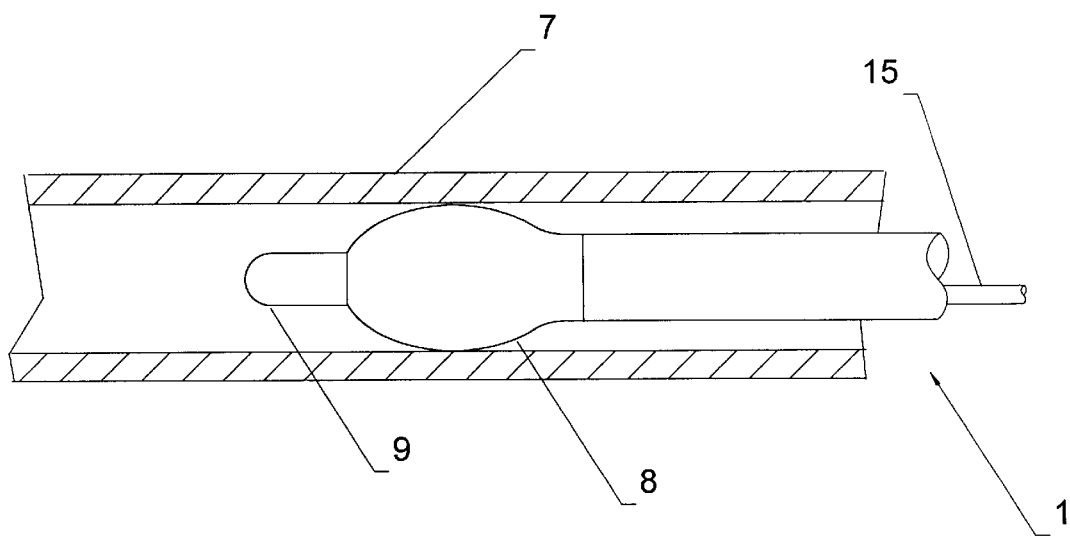
FIG. 2 is a view of a system according to the present invention implanted in a coronary vein.

As illustrated in FIG. 2., the lead system 1 is lodged in position such that the lead system 1 can occlude blood flow in the coronary vein 7. Blood flow can be occluded in the coronary vein 7 to ensure that a pressure transducer 9 obtains a hydrostatic pressure of blood in the coronary vein 7.

To enable occlusion, the lead system 1 includes an occlusion device 8 that is located on a distal end of the lead system 1. Depending on the venous implantation path and any guide assistance apparatus used in the implantation procedure, the occlusion device 8 may include an enlarged diameter of the distal end. An enlarged diameter is formed with dimensions such that it can successfully occlude the coronary vein 7 while still allowing the lead system 1 to be advanced unimpeded along the implantation path.

In cases where an enlarged diameter of the lead system 1 cannot be used to occlude the coronary vein 7, alternate configurations of the occlusion device 8 may be used. Alternate occlusion devices 8 include an agent that swells upon fluid contact applied at a distal end of the lead system 1. Absorbable embolic agents such as Gelfoam (gelatin sponge) or Avitene (microfibrillar collagen) can be applied around the periphery of the distal end of a lead system 1 to provide occlusion. The absorbable agent can be combined with a non-absorbable agent such as polyvinyl alcohol (PVA) particles to increase adhesion. Other configurations of an occlusion device 8 may include an inflatable balloon. A balloon can be mounted on the distal end of the lead system 1 and inflated by injection of a fluid within an open lumen of the lead system 1.

The lead system 1, as shown in FIG. 2, includes a pressure transducer 9 at a distal tip. A pressure transducer 9 used in this application can be a micro-electrical-mechanical system (MEMS). MEMS technology uses semiconductor techniques to build microscopic mechanical devices in silicon or similar materials. The pressure transducer 9 can include a micromachined capacitive or piezoresistive transducer exposed to the bloodstream. Other pressure transducer technologies, such as resistive strain gages, are known in the art and can also be employed as a pressure transducer 9. The pressure transducer 9 is coupled to one or more conductors 15 disposed along the length of the lead system 1. In the configuration shown in FIG. 2, the pressure transducer 9 is integrated with the lead system 1.

Figure 3:
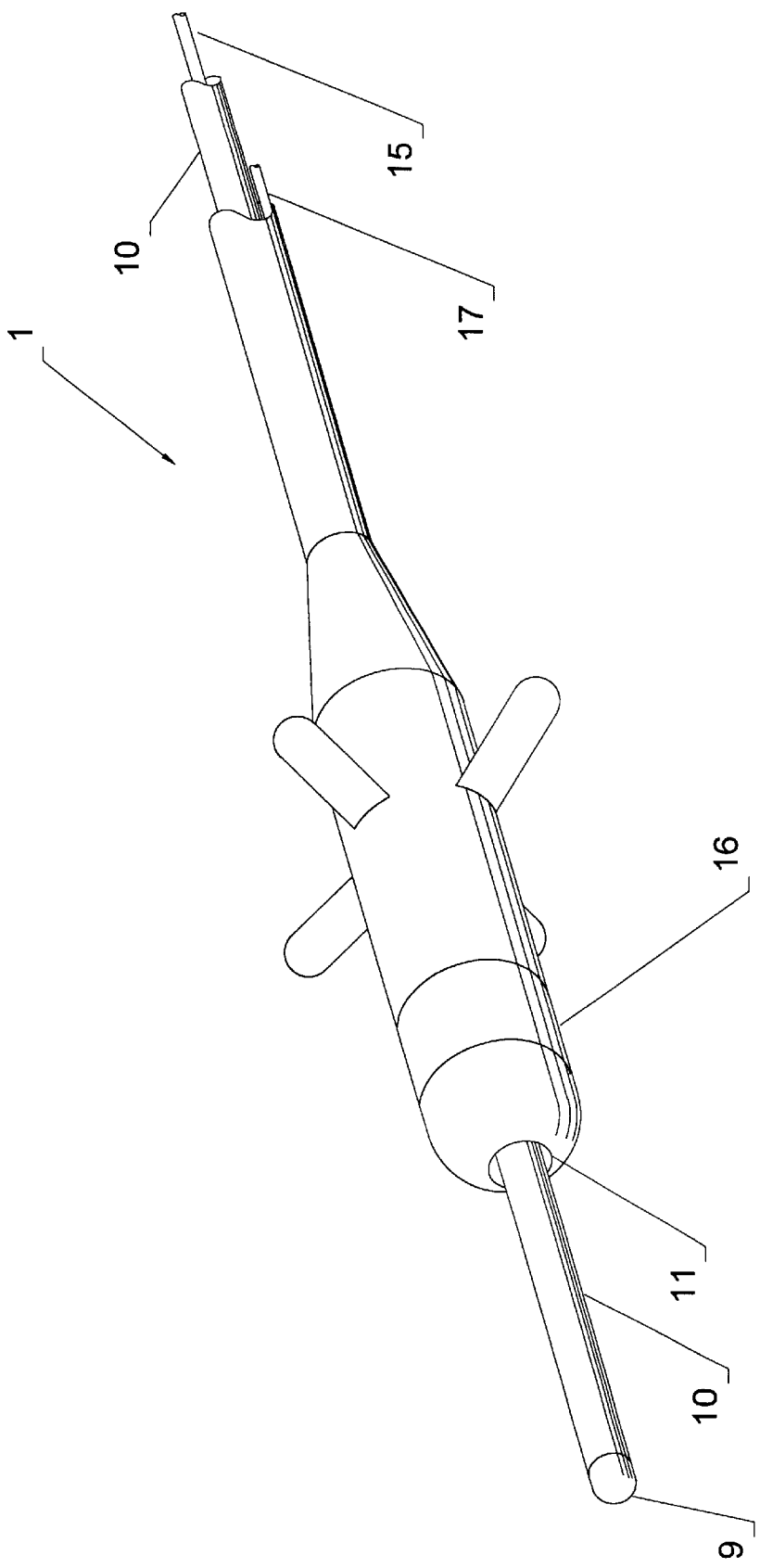
FIG. 3 is an external view of a distal end of an apparatus embodying features of the present invention.

FIG. 3 shows an alternate configuration of a pressure transducer 9. The pressure transducer 9 is mounted to a distal tip of a catheter 10. The catheter 10 is sized such that it can be movably disposed within an open lumen 11 of the lead system 1. The lead system 1 may already include an open lumen 11 for an over-the-wire installation technique. After lead system installation, the catheter 10 can be distally advanced through the lead system 1 until a distal tip of the catheter 10 extends past the distal tip of the lead system 1. This advantageously allows the orientation of the transducer 9 to be adjusted during installation to account for effects such as damping caused by nearby anatomical features. After the catheter 10 has been positioned satisfactorily, it can be secured to the lead system 1 and coupled to the detection/energy delivery system 2 (shown in FIG. 1).

At least one electrode 16 is also disposed on a distal end of the lead system 1. The electrode 16 is utilized to read electrical signals from the heart and apply synchronized electrical impulses to the heart tissue to pace the heart. The electrode is coupled to a conductor 17. In one configuration, two or more electrodes 16 are utilized, with one electrode 16 used for reading electrical signals while other electrodes 16 are used for applying electrical impulses. Construction and use of pacing lead electrodes 16 are well known in the art.

In a system according to the present invention, the electrical impulses delivered to the electrode 16 can be adaptively adjusted by the detection/energy delivery system 2 based on pressure sensor outputs from the pressure transducer 9. This adjustment of the impulses may include a change of pacing rate (e.g., to adapt to changes in activity) or may include a change in the synchronization of electrical signals used to provide CRT (e.g., when reduced pumping capacity is detected).

Figure 4:
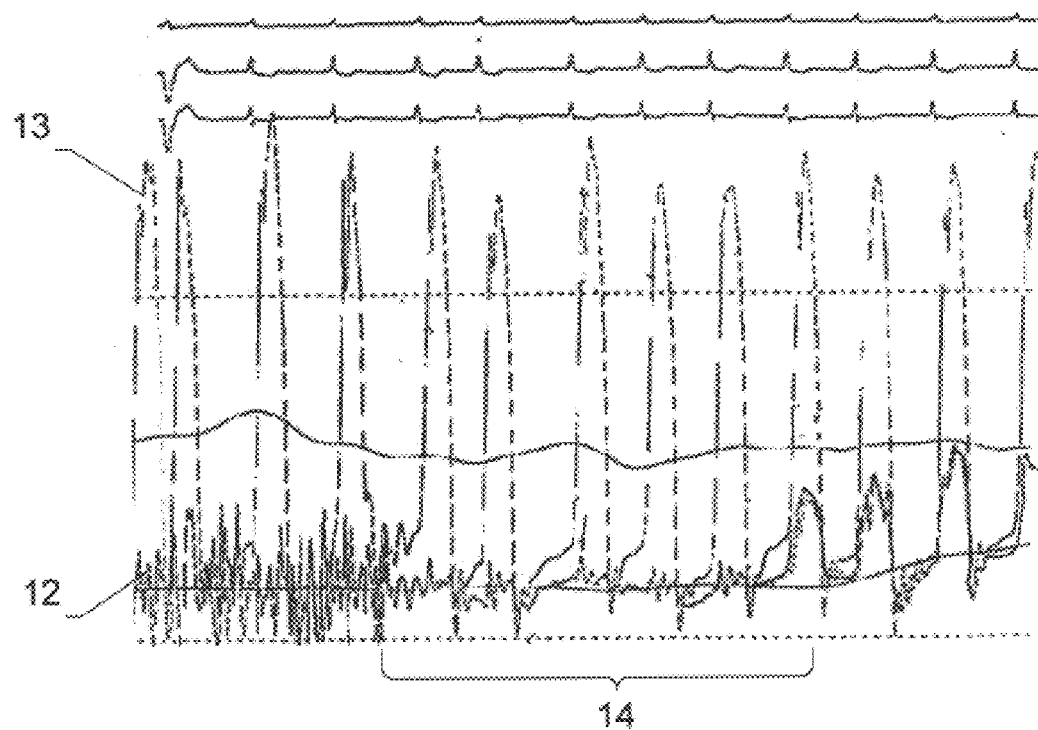
FIG. 4 is an ECG and pressure graph showing a pressure reading from a device according to the present invention overlaid with left ventricular pressure readings, the graph showing the change in coronary vein pressure before and after vein occlusion.

The pressure readings from the pressure transducer 9 in the occluded coronary vein 7 are proportional to LVP. FIG. 4 shows the pressure 12 measured from the coronary vein using a device according to the present invention. The LVP 13 from the same heart is also shown in FIG. 4. Occlusion of the coronary vein occurs in the region 14 shown in FIG. 4. Note that prior to occlusion, the coronary vein pressure 12 is random, corresponding to dynamic pressure of turbulent flow within the vein. After occlusion, the pressure 12 is a hydrostatic pressure reading that is proportional to the LVP 13.

Figure 5:
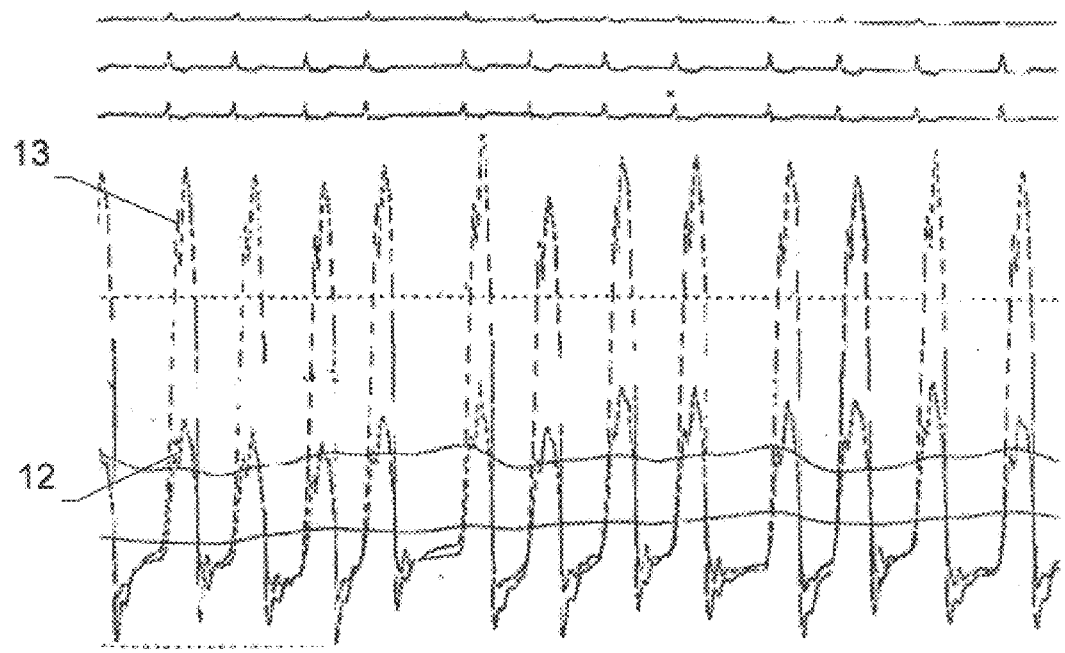
FIG. 5 is an ECG and pressure graph showing a steady-state pressure reading from a device according to the present invention overlaid with direct left ventricular pressure readings.

In FIG. 5, a steady state, hydrostatic, coronary vein pressure 12 is shown superimposed over the LVP 13. The amplitude of the coronary vein pressure 12 is proportional to the LVP 13. The coronary vein pressure 12 faithfully reproduces timing and amplitude variations of the left ventricle systolic pressure. In cases where actual LVP 13 values are desired, the reading of coronary vein pressure 12 can be adjusted with a scaling factor. The scaling factor can be determined after lead installation by using a cuff reading or by using an invasive arterial method to measure actual LVP 13. The measured LVP 13 is compared versus coronary vein pressure 12 to derive the scaling factor. The scaling factor can be input to the detection/energy delivery system 2 and used for processing of pressure transducer readings.

Measuring LVP with a device according to the present invention provides other benefits for applying CHF therapies. For example, in cardiac therapy using bi-ventricular pacing (e.g., CRT), benefits are obtained from synchronizing the contractions of the right and left ventricle using pacing electrodes. If a method or apparatus for acquiring a right ventricular pressure (RVP) signal is provided (for example, via a pressure transducer incorporated into a right ventricular pacing lead) and the left ventricular pressure signal is acquired from a coronary venous lead, the degree of synchronization of these two chambers can be assessed by plotting RVP versus the LVP and determining the area of the resulting approximately elliptical shape. This elliptical shape is referred to as a PP Loop.

A method and apparatus for using the PP Loop for characterizing therapy for CHF patients is described in commonly owned U.S. Pat. No. 6,280,389, which is hereby incorporated herein by reference. A given parameter (e.g., atrioventricular delay or interventricular delay) associated with CRT may be optimized by varying the parameter(s) to minimize the PP Loop area. This process can be carried out periodically to correct for physiological changes which may occur in the course of the disease or therapy. Alternatively, these parameters may be adjusted to generate a desired time or phase delay between the right and left ventricular pressure signals. The relative timing or phase of these pressure signals may be extracted by analysis of maximum or minimum threshold values from time domain pressure readings. Relative phasing can also be determined from the frequency domain by analyzing the fundamental of a Fourier analysis, such as by use of a Fast Fourier Transform (e.g., FFT) analysis. The computation required to perform FFT and/or extract timing values from pressure signals is known in the art and can be readily implemented in the detector/energy delivery system 2.

Referring back to FIG. 1, an exemplary second lead system 18 for measuring right ventricular pressure is shown deployed in the right ventricle. The second lead system 18 can include pressure transducers and electrodes similar to the configurations described for the lead system 1. The second lead system 18 is coupled to the detector/energy delivery system 2, and can provide RVP readings useful for deriving a PP Loop. The second lead system 18 can also sense and deliver electrical signals useful for therapies such as CRT.

Another benefit provided by the present invention relates to the ability to provide electromechanical timing. Electromechanical timing may be continuously assessed by measuring the time interval between an electrical event (for example, the beginning of an R-wave) and a mechanical event such as the beginning of an increase in LVP measured with a coronary venous pressure transducer during isovolumic contraction. This interval, called the pre-ejection period or PEP, is related to sympathetic nervous activation and may be used to control pacing rate or other CRT parameters (e.g., atrioventricular delay or interventricular delay). An apparatus for controlling pacing parameters based on PEP is described in commonly owned U.S. Pat. No. 4,773,401, which is hereby incorporated herein by reference.

A system according to the present invention can provide improved therapy by adjusting pacing parameters to minimize the PEP. When the isovolumic contraction time, which is the variable component of the PEP, reaches a minimum value, the left ventricular mechanical activation is occurring in the most synchronous fashion and the contraction is, therefore, most mechanically efficient. This optimization is ideally carried out at rest under otherwise steady state conditions because variations in PEP due to activation of the sympathetic nervous system could confuse the outcome.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A body implantable system, comprising:
    a lead system comprising an open lumen, at least one electrode, and an occlusion device at a distal end of the lead system;
    a sensing catheter movably disposed within the open lumen of the lead system, a distal tip of the sensing catheter extendable beyond a distal tip of the lead system, the sensing catheter comprising at least one pressure transducer at a distal end of the sensing catheter; and
    a detection/energy delivery system coupled to the lead system, the detection/energy delivery system sensing ventricular rhythms from the at least one electrode, sensing hydrostatic pressure from the at least one pressure transducer, and delivering an electrical signal to the at least one electrode.

2. The system of claim 1, wherein the pressure transducer comprises a capacitive pressure sensor.

3. The system of claim 1, wherein the pressure transducer comprises a piezoresistive pressure sensor.

4. The system of claim 1, wherein the pressure transducer comprises a MEMS pressure sensor.

5. The system of claim 1, wherein the pressure transducer comprises a resistive pressure sensor.

6. The system of claim 1, wherein the detection/energy system delivers a synchronized electrical signal to the at least one electrode for resynchronization therapy.

7. The system of claim 1, wherein the detection/energy system uses a measured pressure from the at least one pressure transducer to adaptively modify the electrical signal sent to the at least one electrode.

8. The system of claim 1, wherein the occlusion device comprises an increased diameter of the lead system at the distal end of the lead system.

9. The system of claim 1, wherein the occlusion device comprises an inflatable member at the distal end of the lead system.

10. The system of claim 9, wherein the inflatable member comprises an absorbable material, the absorbable material inflating upon contact with a fluid.

11. The system of claim 9, wherein the inflatable member inflates by injection of a fluid into the lead system.

12. A method of pacing a patient's heart, comprising:
    providing a lead system disposed within a coronary vein of the patient's heart, the lead system comprising:
    an open lumen;
    at least one electrode; and
    an occlusion device at a distal end of the lead system;
    introducing a sensing catheter within the open lumen of the lead system until a distal tip of the sensing catheter extends beyond a distal tip of the lead system, the sensing catheter comprising at least one pressure transducer at a distal end of the sensing catheter;
    measuring ventricular electrical rhythms from the at least one electrode to deliver a synchronized electrical signal to the at least one electrode; and
    measuring, while occluding blood flow in the vein using the occlusion device, a coronary vein pressure from the pressure transducer to adaptively modify the synchronized electrical signal.

13. The method of claim 12, further comprising measuring a right ventricular pressure prior to adaptively modifying the synchronized electrical signal, and wherein adaptively modifying the synchronized electrical signals further comprises adaptively modifying the synchronized electrical signals to minimize an area of a PP loop derived from the measured right ventricular pressure and the measured coronary vein pressure.

14. The method of claim 12, wherein modifying the synchronized electrical signal further comprises measuring a timing between the measured coronary vein pressure and the measured ventricular electrical rhythms.

15. The method of claim 14, wherein modifying the synchronized electrical signal further comprises modifying the synchronized electrical signal to minimize the pre-ejection period.

16. The method of claim 12, wherein the pressure transducer comprises a MEMS pressure sensor.

17. The method of claim 12, wherein the pressure transducer comprises a resistive pressure sensor.

18. The method of claim 12, wherein the pressure transducer comprises a capacitive pressure sensor.

19. The method of claim 12, wherein the pressure transducer comprises a piezoresistive pressure sensor.

20. The method of claim 12, wherein the occlusion device comprises an increased diameter at the distal end of the lead system.

21. The method of claim 12, wherein the occlusion device comprises an inflatable member at the distal end of the lead system.

22. The method of claim 21, wherein the inflatable member comprises an absorbable material, the absorbable material inflating upon contact with a fluid.

23. The method of claim 21, wherein the inflatable member inflates by injection of a fluid into the lead system.

24. The method of claim 12, further comprising calculating a scaling factor based on a measured coronary vein pressure and a left ventricular pressure after introducing the sensing catheter, and wherein adaptively modifying the rate of the synchronized electrical signal further comprises applying the scaling factor to the measured coronary vein pressure.

25. A method of pacing a patient's heart, comprising:
   implanting a first lead system into a coronary vein of the patient's heart and a second lead system into a chamber of the patient's heart, the first and second lead systems each comprising:
   at least one electrode; and
   at least one pressure transducer at a distal end of the lead system; measuring ventricular electrical rhythms from the respective electrodes of the first and second lead systems to deliver synchronized electrical signals to the respective electrodes of the first and second lead systems; and
   measuring a coronary vein pressure from the at least one pressure transducer of the first lead system and measuring a heart chamber pressure from the at least one pressure transducer of the second lead system to adaptively modify the synchronized electrical signals.

26. The method of claim 25, wherein the second lead system is implanted in the right ventricle, and wherein adaptively modifying the synchronized electrical signals further comprises measuring a right ventricular pressure from the at least one pressure transducer of the second lead system.

27. The method of claim 26, wherein adaptively modifying the synchronized electrical signals further comprises adaptively modifying the synchronized electrical signals to minimize an area of a PP loop derived from the measured right ventricular pressure and the measured coronary vein pressure.

28. The method of claim 25, wherein modifying the synchronized electrical signals further comprises measuring a timing between the measured coronary vein pressure and the measured ventricular electrical rhythms.

29. The method of claim 28, wherein modifying the synchronized electrical signal further comprises modifying the synchronized electrical signal to minimize the pre-ejection period.

30. The method of claim 25, wherein modifying the synchronized electrical signals further comprises measuring a timing between the measured heart chamber pressure and the measured ventricular electrical rhythms.

31. The method of claim 30, wherein modifying the synchronized electrical signal further comprises modifying the synchronized electrical signal to optimize an electromechanical timing period.

32. The method of claim 25, wherein the pressure transducer comprises a MEMS pressure sensor.

33. The method of claim 25, wherein the pressure transducer comprises a resistive pressure sensor.

34. The method of claim 25, wherein the pressure transducer comprises a capacitive pressure sensor.

35. The method of claim 25, wherein the pressure transducer comprises a piezoresistive pressure sensor.

36. The method of claim 25, further comprising calculating a scaling factor based on a measured coronary vein pressure and a left ventricular pressure after implanting a first lead system, and wherein adaptively modifying the rate of the synchronized electrical signals further comprises applying the scaling factor to the measured coronary vein pressure.

* * * * *